United States Patent [19]

Saunders

[11] 3,937,069

[45] Feb. 10, 1976

[54] HARDNESS TESTER

[75] Inventor: Frank L. Saunders, Midland, Mich.

[73] Assignee: The Dow Chemical Company, Midland, Mich.

[22] Filed: Mar. 28, 1975

[21] Appl. No.: 563,038

[52] U.S. Cl. .................................. 73/81; 73/150 R
[51] Int. Cl.[2] .................................. G01N 3/42
[58] Field of Search........ 73/81, 150 R, 150 A, 104, 73/85, 78

[56] References Cited
UNITED STATES PATENTS

| | | | |
|---|---|---|---|
| 2,279,264 | 4/1942 | Hoffman | 73/78 |
| 3,389,463 | 6/1968 | Gerek et al. | 73/150 X |

Primary Examiner—Jerry W. Myracle
Attorney, Agent, or Firm—Earl D. Ayers

[57] ABSTRACT

The tester comprises basically a four wheeled carriage, a scale arm containing graduations attached to the carriage in a counterpoised condition about a pivot axis, and a rolling, round fluted cutting tool coupled to the carriage and to the scale arm. The cutting tool, as the carriage is drawn across a test surface, leaves an indented track of the cutting flutes. The width of the track marks is a function of the coating hardness and applied load.

3 Claims, 4 Drawing Figures

HARDNESS TESTER

BACKGROUND OF THE INVENTION

This invention relates to hardness testers and particularly to an instrument for measuring coating hardness.

One such device is the Hoffman Scratch-Hardness Tester sold by Gardner Laboratory Incorporated (Catalog No. SG-1610-M). The original tester is described in U.S Pat. No. 2,279,264 and the current model is a slight modification of this device. It consists basically of a four-wheeled carriage; a scale arm graduated from 0-20 that is attached permanently to the carriage in a counter-poised condition about the pivot axis; and a scratching tool with a sharp circular mounted mouned at 45° to the test surface. In operation small and/or large riders are attached to the scale arm at the numbered positions. The carriage is held down firmly by hand and moved in the opposite direction to cause a trailing scratch. The larger rider generates a load of 100 grams per division, while the small rider generates a load of 25 grams per division. The tester is placed on a reasonably flat, level, test surface that measures at least 2 in. × 4 in.

The thumb and first two fingers of the right hand are placed on the carriage platform, directly over the pair of wheels nearest the scratching tool, using sufficient downward pressure to lift the counterpoised beam with the selected rider at the 0 position. The tester is pulled to the right in a straight line across the test surface, making sure that the scratching tool follows the rolling carriage.

The scratch resistance is measured by increasing the load by moving the rider to the left and observing the load necessary to make just a preceptible mark or scratch on the coating. As an alternate procedure, the width and character of the scratch made on a series of test surfaces with the same load are compared. A measuring microscope facilitates the measurement.

However, in use, polymer scratched from the coating often accumulates on the scratching tool causing erratic results and poor scratch definition.

OBJECTS OF THE INVENTION

A principal object of this invention is to provide an improved hardness tester for coatings. Another object of this invention is to provide an improved, substantially non-scratching hardness tester for use with polymeric coatings.

STATEMENT OF INVENTION

In accordance with this invention the scratching tool of a hardness tester of the Hoffman Scratch-Hardness Tester type is replaced by a rolling round fluted cutting tool which when rolled over the coating under load as described above leaves an indented track of the cutting flutes. The width of the track marks is a function of the coating hardness and applied load. The nature of the cutting tool will also influence the track width, its sharpness and radius of cutting flutes. A convenient marking tool is a round ¼ inch diameter cutting tool with 12 cutting flutes connected to a ⅛ inch shaft. In making a test measurement, one revolution of the tool leaves 12 marks which are measured with a measuring microscope and averaged to give a number representing the penetration of the tool, and related to hardness.

This improved tester has eliminated the polymer build-up and can be used to measure relative hardness of coatings and polymer surfaces. Comparison between various coatings of similar thickness can be made by making measurements under a fixed load. The load is chosen to produce a perceptible mark on the coating but not sufficient to completely cut the coating to the base substrate.

BRIEF DESCRIPTION OF THE DRAWING

The above objects, as well as additional objects and advantages of this invention will be understood when the following detailed description is read in connection with the accompanying drawing, in which.

DETAILED DESCRIPTION OF THE DRAWING

Figure 1:
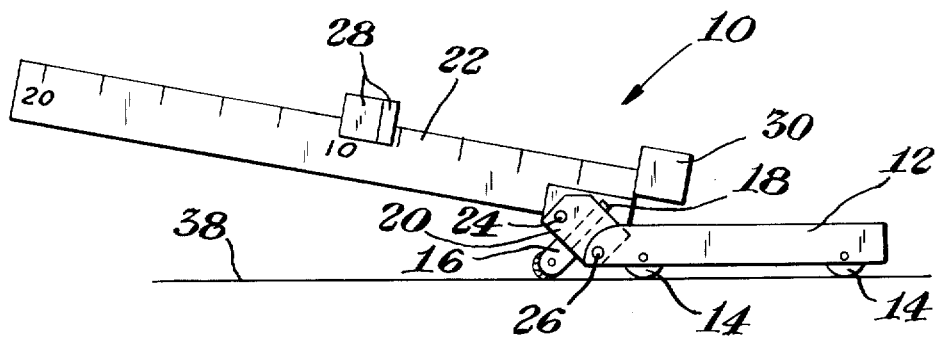
FIG. 1 is a simplified side elevational view of a hardnss tester in accordance with this invention.

Referring to the drawing, there is shown a hardness tester 10 comprising a block like carriage 12 having wheels 14 at each side, front and rear, of the carriage 12, a scale arm 22 which is pivotally coupled to the rear of the carriage 12 by the pin 26. The pin 26 extends through a coupler element 20 which contains a bore into which the shaft 18 of the tool carrier body 16 fits. The wall of the bore into which the shaft 18 fits is split and may be compressed by means of the screw 24 which extends into the coupler element 20.

Slidable weights 28 are carried on the calibrated scale arm 22.

Figure 4:
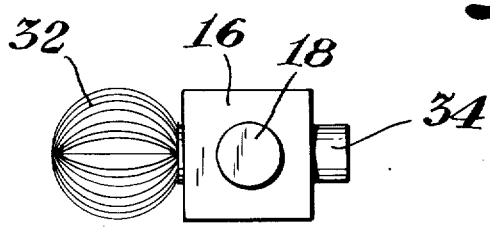
FIG. 4 is a plan view of the tool assembly of FIG. 2.
Figure 3:
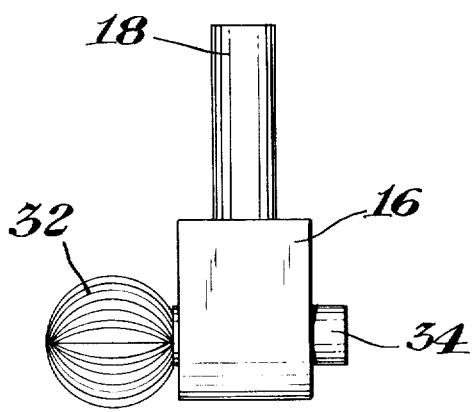
FIG. 3 is in end elevational view of the tool assembly of FIG. 2.
Figure 2:
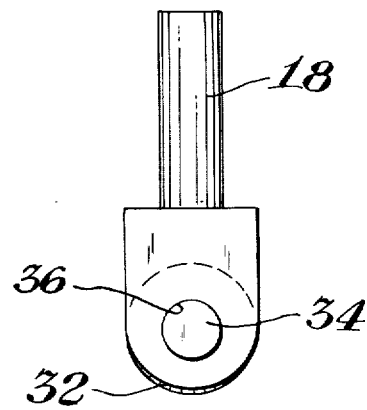
FIG. 2 is a side elevational view of the fluting tool assembly of the apparatus of FIG. 1.

Referring now to FIGS. 2, 3 and 4 as well as to FIG. 1, the tool carrier body 16 is a block-like element which has a shaft 18 extending from one end and a bore 36 extending through the body perpendicularly with respect to the shaft 18.

A ball-like fluting element 32 containing a continuous array of cutting flutes has its shaft 34 extending through the bore 36 in a slidable relationship with the walls of that bore.

Operation

In operation small and/or large riders 28 and counter weights 30, for example, are attached to the scale arm 22. The carriage 12 is held down firmly by hand and moved in the opposite direction to cause trailing indentations on the test surface 38. The riders 28 generate a load of 100 grams per division, or a load of 25 grams per division. The tester 10 is placed on a reasonably flat, level, test surface that measures at least 2 inches × 4 inches. The thumb and first two fingers of the right hand are placed on the carriage 12, directly over the pair of wheels nearest the fluting tool 32, using sufficient downward pressure to lift the couterpoised beam arm 22 with the selected rider 28 at the 0 position. The tester is pulled to the right in a straight line across the test surface, making sure that the fluting tool follows the rolling carriage.

As the rolling round fluted cutting tool 32 passes over the coating being tested, it leaves on the surface an indented track of the flutes of the tool 32. The width of the track marks is a function of the coating hardness and applied load.

The nature of the cutting tool 32 will also influence the track width, its sharpness and radius of cutting flutes. A convenient tool 32 is a round ¼ inch diameter cutting tool with 12 cutting flutes connected to a ⅛ inch shaft 34. In making a test measurement, one revolution of the tool leaves 12 marks which are measured with a measuring microscope and averaged to give a number representing the penetration of the tool, and related to hardness.

The tester of this invention has eliminated the polymer build-up which occurred when a scratching tool was used and can be used to measure relative hardness of coatings and polymer surfaces. Comparison between various coatings of similar thickness can be made by making masurements under a fixed load. The load is chosen to produce a perceptible mark on the coating but not sufficient to completely cut the coating to the base substrate.

As an example of how this device 10 can be used, the following measurements were made on a thermosetting acrylic finish applied to a steel test panel. The testing device was rolled over the surface of the coating increasing the load on the cutting tool as described above. The width of the indentations was measured with a 40X measuring microscope, the average of the 12 marks for each load recorded and listed in Table I.

TABLE I

| Load, Grams | Average Width of Track, Div. |
|---|---|
| 400 | 7.3 ± 0.9 |
| 600 | 11.3 ± 0.9 |
| 800 | 13.3 ± 0.8 |
| 1000 | 14.3 ± 1.0 |
| 1200 | 15.3 ± 0.8 |
| 1500 | 16.8 ± 1.1 |
| 2000 | 17.9 ± 0.8 |
| 1 Div. = .022" | |

Similar measurements were made on a ⅛ inch thick polymethyl methacrylate sheet, Acrylite, American Cyanamid Company.

| Load, Grams | Average Width of Track, Div. |
|---|---|
| 1000 | 10.8 ± 0.6 |
| 1500 | 13.7 ± 0.5 |
| 2000 | 16.2 ± 0.7 |

The indentions in the coating may be filled with a black wax pencil or wiped with an ink to improve the resolution of the marks.

I claim:

1. In a hardness tester comprising a four wheeled carriage having a scale arm pivotally mounted from one end thereof and supporting a pressure application member in a fixed position with respect to said scale arm whereby said pressure application member contacts a surface to be tested when said wheeled carriage is rolled along said surface, the improvement wherein:

said pressure application member comprises a ball-like fluted member mounted to rotate along a line which is parallel to any forward movement of said wheeled carriage.

2. Apparatus in accordance with claim 1, wherein said fluted member has a shaft connected to one side thereof, said shaft being rotatably coupled to said scale arm.

3. Apparatus in accordance with claim 1, wherein said scale arm and said pressure application member are each fixed positionally coupled to a coupling member which is pivotally coupled to said carriage.

* * * * *

UNITED STATES PATENT AND TRADEMARK OFFICE
CERTIFICATE OF CORRECTION

PATENT NO. : 3,937,069

DATED : February 10, 1976

INVENTOR(S) : Frank L. Saunders

It is certified that error appears in the above—identified patent and that said Letters Patent are hereby corrected as shown below:

In column 1, line 15, insert the word --rim-- after the word "circular".

In column 1, line 15, delete the word "mouned", the last word in the line.

In column 2, line 14, delete "hardnss" and insert --hardness--.

In column 3, line 12, delete "masurements" and insert --measurements--.

In column 3, Table 1, last line of first column headed "Load. Grams", delete ".022" ", and insert --.002--.

Signed and Sealed this

Seventeenth Day of August 1976

[SEAL]

Attest:

RUTH C. MASON
*Attesting Officer*

C. MARSHALL DANN
*Commissioner of Patents and Trademarks*